(12) United States Patent
Gallant

(10) Patent No.: US 9,757,549 B2
(45) Date of Patent: Sep. 12, 2017

(54) DEVICE AND METHOD FOR INSERTING LUBRICATING CAPSULE

(71) Applicant: Esther Gallant, Newport Beach, CA (US)

(72) Inventor: Esther Gallant, Newport Beach, CA (US)

( * ) Notice: Subject to any disclaimer, the term of this patent is extended or adjusted under 35 U.S.C. 154(b) by 0 days.

(21) Appl. No.: 15/008,037

(22) Filed: Jan. 27, 2016

(65) Prior Publication Data

US 2016/0136403 A1    May 19, 2016

Related U.S. Application Data

(63) Continuation of application No. 14/107,955, filed on Dec. 16, 2013, now Pat. No. 9,272,123.

(51) Int. Cl.
*A61M 31/00* (2006.01)
*A61F 13/26* (2006.01)
*A61H 19/00* (2006.01)

(52) U.S. Cl.
CPC .......... *A61M 31/007* (2013.01); *A61F 13/266* (2013.01); *A61H 19/44* (2013.01); *A61H 2201/105* (2013.01)

(58) Field of Classification Search
CPC ............ A61M 31/007; A61M 15/0035; A61M 15/0041; A61F 13/266
See application file for complete search history.

(56) References Cited

U.S. PATENT DOCUMENTS

| | | | | |
|---|---|---|---|---|
| 3,786,820 A | * | 1/1974 | Kopfer | A45D 34/042 132/74.5 |
| 4,808,166 A | | 2/1989 | Davidov | |
| 4,995,385 A | * | 2/1991 | Valentini | A61M 15/0028 128/203.15 |
| 5,152,284 A | * | 10/1992 | Valentini | A61M 15/0028 128/203.12 |
| 5,542,914 A | | 8/1996 | Van Iten | |

(Continued)

FOREIGN PATENT DOCUMENTS

| | | |
|---|---|---|
| DE | 19922537 A1 | 11/2000 |
| GB | 2417231 A | 2/2006 |
| JP | 09028805 A * | 2/1997 |

OTHER PUBLICATIONS (Ray, L) "Over the Counter Products to Treat Vaginal Dryness" livestrong.com, Mar. 11, 2011 International Search Report dated Apr. 30, 2015 by US/ISA.

(Continued)

*Primary Examiner* — Susan Su
(74) *Attorney, Agent, or Firm* — Fulwider Patton LLP

(57) ABSTRACT

An applicator for insertion and lubrication of a body lumen is disclosed having an elongate, hollow, cylindrical outer sheath including a receiving cup at a distal end for receiving a lubrication capsule; and a plunger slidingly received within the elongate, hollow cylindrical outer sheath, the plunger including a piercing element at a distal end adapted to extend into the receiving cup. A liquid-filled soft gel capsule is placed in the receiving cup, and the piercing element is used to puncture the capsule located in the receiving cup prior to insertion of the applicator into the body lumen, and wherein the plunger can be depressed once the applicator is inserted into the body lumen to eject the pierced capsule into the body lumen.

1 Claim, 3 Drawing Sheets

(56) References Cited

U.S. PATENT DOCUMENTS

| | | | | |
|---|---|---|---|---|
| 5,673,686 A | * | 10/1997 | Villax | A61M 15/0028 128/203.12 |
| 5,989,217 A | * | 11/1999 | Ohki | A61M 15/0028 128/200.22 |
| 6,746,420 B1 | * | 6/2004 | Prestidge | A61M 25/0631 604/158 |
| 6,971,385 B1 | * | 12/2005 | Flora | A61M 15/0028 128/203.21 |
| 7,172,573 B1 | * | 2/2007 | Lamb | A61M 31/007 604/11 |
| 7,666,160 B2 | | 2/2010 | Rajala et al. | |
| 8,869,794 B1 | * | 10/2014 | Tuckwell | A61M 15/0041 128/203.21 |
| 2004/0078013 A1 | | 4/2004 | Zunker et al. | |
| 2005/0000518 A1 | * | 1/2005 | Dunkley | A61M 15/0028 128/203.21 |
| 2005/0022813 A1 | * | 2/2005 | Alston | A61M 15/0028 128/203.21 |
| 2005/0056280 A1 | * | 3/2005 | Alston | A61M 15/0028 128/203.21 |
| 2006/0173405 A1 | | 8/2006 | Haithcock | |
| 2007/0032758 A1 | | 2/2007 | Chase et al. | |
| 2007/0060998 A1 | | 3/2007 | Butterwick et al. | |
| 2007/0129668 A1 | | 6/2007 | Swick | |
| 2007/0221216 A1 | * | 9/2007 | Ganem | A61M 15/0028 128/203.12 |
| 2007/0240713 A1 | * | 10/2007 | Boeck | A61M 15/0028 128/203.15 |
| 2007/0281008 A1 | | 12/2007 | Lin et al. | |
| 2009/0155354 A1 | | 6/2009 | McLean et al. | |
| 2009/0326375 A1 | | 12/2009 | Magee | |
| 2009/0326475 A1 | | 12/2009 | Carlyon | |
| 2011/0005535 A1 | * | 1/2011 | Xiu | A24F 47/008 131/273 |
| 2011/0067707 A1 | | 3/2011 | Hui | |
| 2011/0073117 A1 | | 3/2011 | Hui | |
| 2011/0220234 A1 | * | 9/2011 | Haas | A61M 15/0028 138/109 |
| 2011/0277752 A1 | * | 11/2011 | Cheu | A61M 15/0028 128/200.14 |
| 2012/0041379 A1 | * | 2/2012 | Macarthur | A61M 5/282 604/192 |

OTHER PUBLICATIONS

Ray L "Over the Counter Products to Treat Vagina Dryness" livestrong.com Mar. 11, 2011 www.livestrong.com/article/32078-over-counter-products-treat-vaginal/.

PCT/US14/70393 with International Filing Date of Dec. 15, 2014.

* cited by examiner

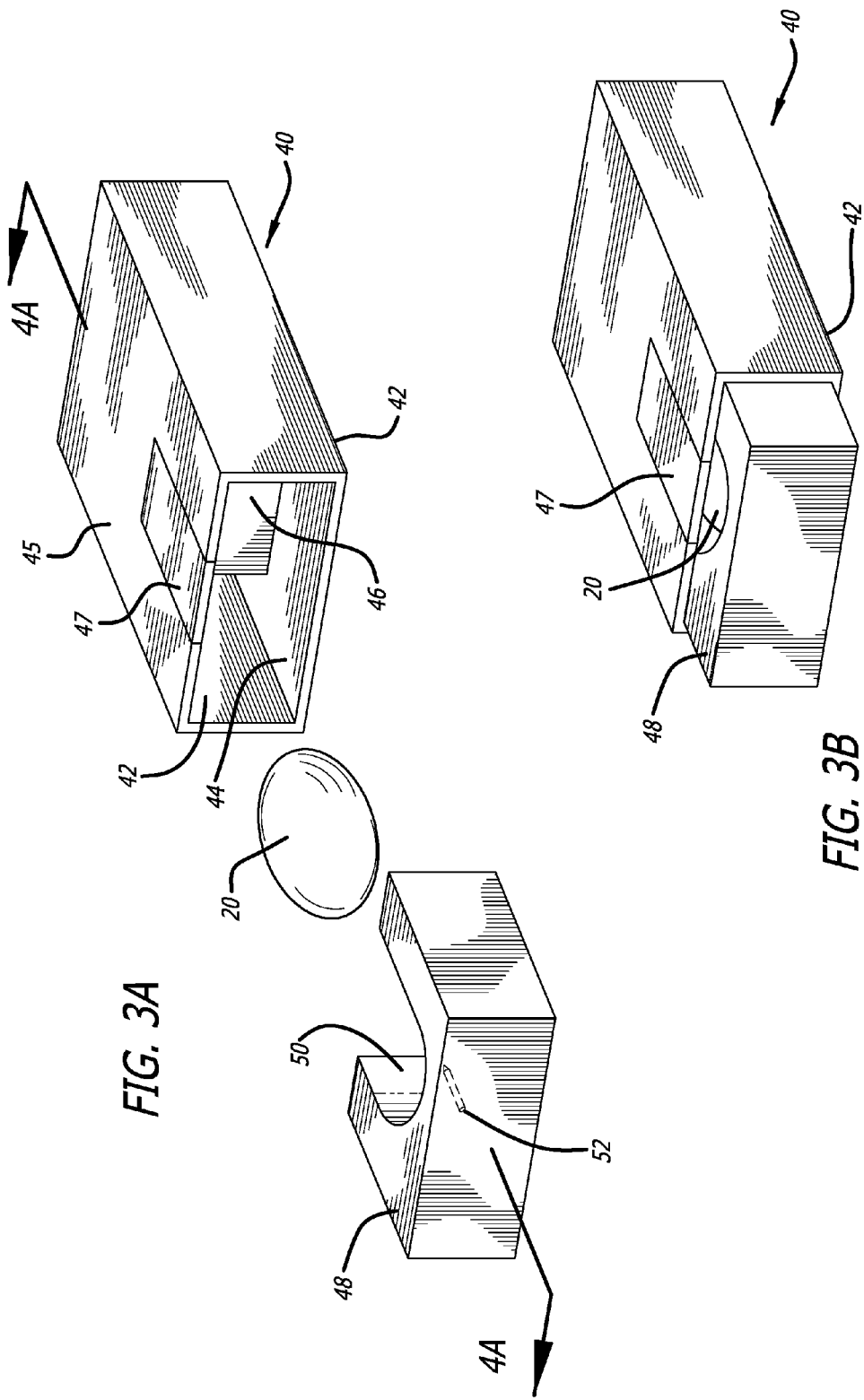

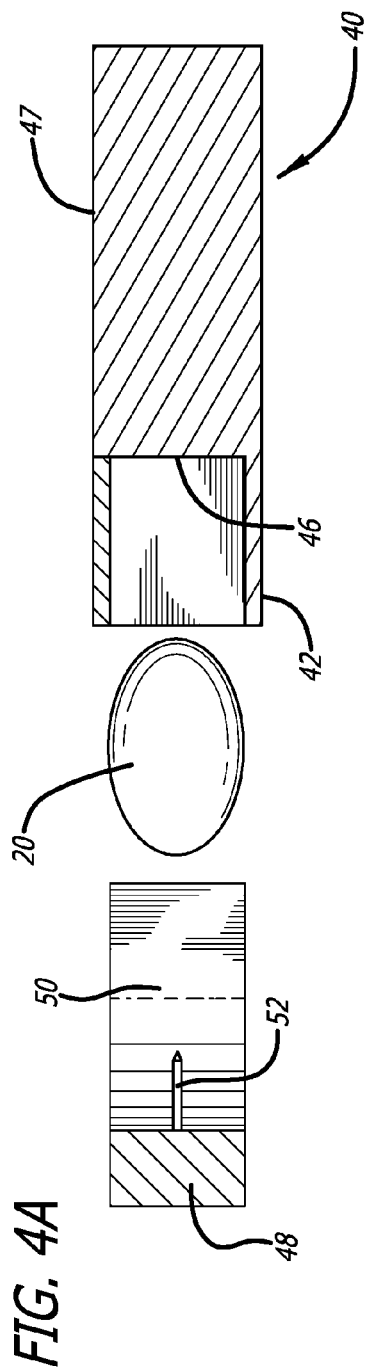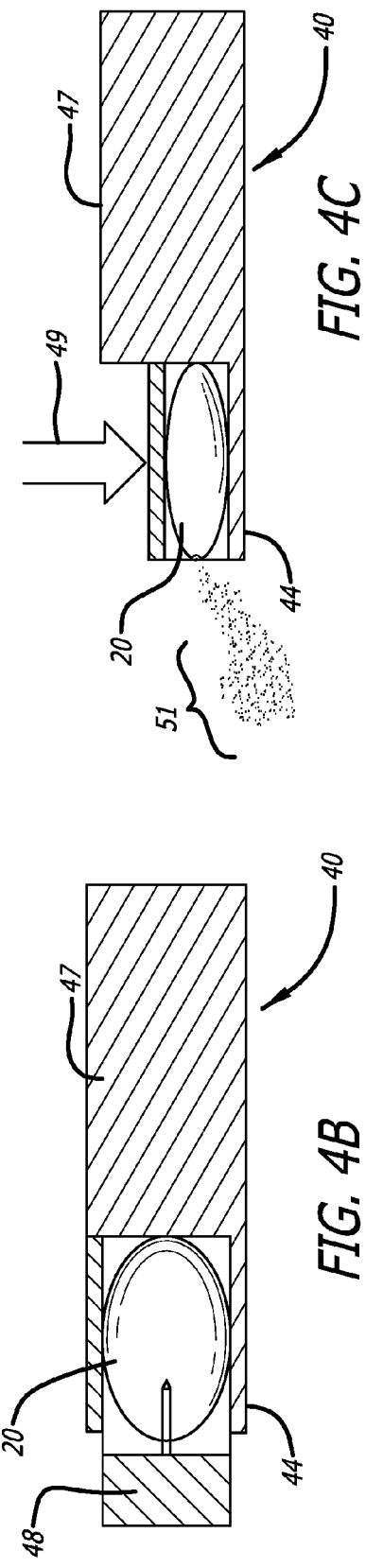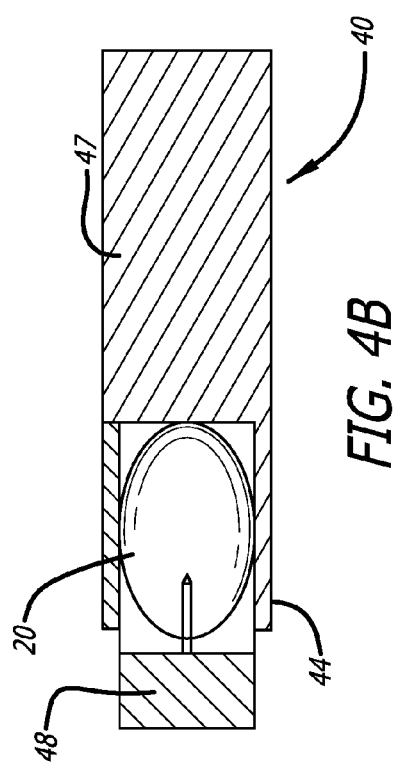

DEVICE AND METHOD FOR INSERTING LUBRICATING CAPSULE

CROSS-REFERENCES TO RELATED APPLICATIONS

This application is a continuation based on U.S. Ser. No. 14/107,955, filed on Dec. 16, 2013, which is incorporated by reference in its entirety herein.

BACKGROUND

Sexual intercourse is a rewarding part of a healthy and active adult life. In the case of vaginal intercourse, the female physiology is particularly suited to facilitate the act through various changes that take place in the female reproductive system, including lengthening of the vaginal canal, contraction of the muscles surrounding the vagina, and secretions of several glands at the back of the vagina, secretions (sweating) directly from the interior vaginal wall, and secretion of the Bartholins glands at the entrance of the vagina, which secrete relatively minute amounts of fluid (one or two droplets of fluid when the female is sexually aroused). These minute droplets of fluid for lubrication were once believed to be important for lubricating the vagina, but research from Masters and Johnson demonstrated that vaginal lubrication comes primarily from deep within the vagina. The (Bartholins gland) fluid may slightly moisten the labial opening of the vagina, serving to make contact with this sensitive area more comfortable for the woman. Given the vast array of commercially available lubricants for external application, it is clear that for a variety of reasons, some herein discussed, the naturally secreted minor lubrication from the labial opening, is insufficient in many cases, to provide adequate lubrication, with the vast majority of secretions coming from deep within the vagina. All of these changes take place in a healthy female and promote a pleasurable experience for each participant.

While these changes in a woman's body occur during intercourse, many women complain about insufficient secretions causing vaginal discomfort and irritation during or after intercourse. In addition to the absence of the frequent vulvo-vaginal inflammatory-infectious conditions, and of the dryness and hypotrophy of these organs resulting from the post-menopausal estrogen fall, one of the causes for this vaginal irritation during and after intercourse, is vaginal penetration before women are adequately aroused. Considering that the first reaction of the female genitals to sexual excitement is vaginal lubrication, if a woman is penetrated without being properly aroused and, therefore, without the occurrence of the necessary physiological vaginal lubrication, several symptoms of vulvo-vaginal discomfort may occur. In addition, even when adequately aroused, many women suffer from insufficient lubrication for a variety of reasons, some of which have already been mentioned. Insufficient lubrication may also cause a degree of discomfort and irritation to the male penis.

Transudation is the process resulting in vaginal lubrication. When a female is sexually aroused, blood flows into the area surrounding the walls of the vagina in a process called vasocongestion. The pressure of the increased blood causes a seepage of moisture from the spaces between the cells. This moisture cresses the vaginal lining, first appearing as tiny droplets. Eventually, the fluid builds up in sufficient quantity to moisten the entire inner walls of the vagina. In the excitement phase, blood flow to the vagina increases which, in turn, pushes fluid into the vaginal canal. This lubricating process allows for comfortable penile insertion, and repetitive insertions during intercourse.

Natural cyclic hormonal alterations, stress, and the use of combined or progestin-only hormonal contraceptives, if applicable, affect the amount and the consistency of vaginal lubrication during normal daily activities and during sexual arousal. Many medications that women use to treat other conditions can adversely affect vaginal lubrication. These medications include antihistamines, anticholinergics, antihypertensives, and most psychoactive agents, particularly SSRIs and benzodiazepines. Women of any age have various reasons for augmenting their natural vaginal secretions with lubricants or moisturizers to facilitate comfort before, during, and after sexual activity. Additionally, repetitive penetration during intercourse may cause the drying out of the lubrication prior to the completion of the activity. Many men, as well as women, also prefer additional lubrication during sexual activity to increase both their and their partner's enjoyment of sexuality.

One problem with traditional methods and products for augmenting the body's natural lubrication system is that the lubricant is applied at the entrance to the vaginal (or anal) opening. This is unsatisfactory for several reasons. The female body's natural lubrication system secretes lubricant from deep inside the body lumen, where the act of intercourse spreads the lubricant along the walls of the vagina. If the lubricant is applied either to the penis or the entrance of the vagina, the large majority of the lubricant is sheared, and wiped off by the penetrating motion of the penis, greatly diminishing the lubricant's usefulness. Existing commercial products to augment a woman's natural lubrication system are applied, at or close to the vaginal opening, and cannot reproduce the body's design to lubricate from well within the body lumen. The present invention is intended to overcome this shortcoming.

SUMMARY OF THE INVENTION

The present invention is a lubrication system and device wherein a soft capsule (generally known as a "gel cap") containing a lubricant therein can be pierced and inserted into a body cavity, where it can leech or drain the lubricant inside the body cavity. Sustained lubricant delivery in situ can occur as a result of muscular contractions around the capsule and/or contact with an object such as a penis. The capsule, which is filled with lubricant material, medicine, or some beneficial substance, or a combination thereof, is preferably made of a bio-absorbable material so that it can be absorbed safely into the body when depleted, similarly to the way a vitamin E gel capsule is absorbed in the body after releasing the contents via oral delivery. The present invention includes a delivery system that both pierces the capsule and then delivers the capsule into a body lumen.

For example, a capsule of lubricant delivered into the vagina, and provided with a small slit or pierced opening, will subsequently seep lubricant as a byproduct of intercourse due to the contraction of the muscles surrounding the vaginal walls and compression as a result of impact with a penis, as well as continuous seepage as a result of the tiny punctured opening created prior to insertion. The lubricant is then forced outward along the walls of the vagina (or anal cavity) by the motion of the penis along with the shape of the head of the penis, whose diameter is larger than the cavity and thus pushes lubricant along the vaginal walls. Thus, throughout the act, lubrication is continuously released from the capsule within the interior of the vagina or body lumen, similar to the body's own lubrication system.

To deliver the lubricant capsule, a two-piece applicator is provided comprising an outer tube of elongate cylindrical construction, with an open plate type bottom, and a plunger type tube which fits inside and slides along the inner length of the outer tube. The plunger may also include an outer plate type bottom, slightly larger than that at the end of the outer tubular section, causing the fully inserted inner tube to "stop" at a premeasured maximum distance. The applicator may incorporate a spring with a biasing force that returns the applicator to the relaxed or undepressed condition. Similar to a mechanical pencil, the inner plunger can be deployed against the bias of the spring, and then when released the spring will return the plunger to the original position. In this manner, the user can eject the capsule from its confines at the distal end in a controlled manner, and the retraction of the plunger by the spring ensures that the pin will safely withdraw from the capsule as it is ejected.

The inner tube has at its distal end a cavity or cup for capturing (or holding) the capsule. Inside the receiving cup is a pin, multiple tiny pins, tiny blade, or other object(s) capable of creating a puncture in the gel capsule. The puncturing device is placed well within the concave cup to avoid contact with any body tissue. The larger bottom plate of the inner tubular plunger causes a "stopping" point and prevents it from exposing the pin (or other piercing device), from coming into contact with any body tissue, and prevents it from causing injury to any body tissue. The gel capsule is then manually placed inside the cup, and with minor pressure is pushed onto the pin (or other piercing device), thereby causing a rupture sufficient to allow the contained material to leak or seep out, once it is inserted well within the vagina. The plunger when fully extended in the body lumen will release the capsule safely, and well within the body lumen. The applicator may be provided with a spring loaded, or push release mechanism in the plunger to eject the capsule from the receiving cup once the applicator is inserted into a body lumen. That is, the applicator is inserted into, for example, a vagina with the capsule positioned on a the distal end within the receiving cup. The plunger is then actuated, which pushes the capsule free of the receiving cup, allowing the capsule to be inserted into the back of the vagina distanced from the vaginal opening with the capsule's piercing oriented toward the opening of the body lumen. The capsule, having been pierced, will slowly leak its contents into the vagina. When the head of the penis (or other object) makes contact with the capsule, additional small amounts of lubricant are released through the tiny opening(s) to continuously lubricate the vaginal walls. In this manner, intercourse can be made more pleasant and enjoyable, eliminating the discomfort of dryness for those who require or desire supplemental lubrication. The capsule itself, being a biocompatible dissolving material (similar to a Vitamin E gel cap) will safely "melt" or "dissolve" inside the body lumen, both providing additional lubricating material, and be absorbed without consequence. If there is anything left of it after the completion of the session of intercourse, if desired, it may be easily removed manually.

It is envisioned that the capsule piercing concept will fulfill additional beneficial purposes, including aiding individuals who cannot swallow, or dislike swallowing, capsules. This invention will make it possible for individuals to consume the contents of capsules by piercing a capsule, simply chewing gently on a pierced gel capsule just a few times, and then discarding the casing. Currently there are devices for crushing or cutting tablets, but many medicines, vitamins, nutritional supplements, etc., come contained in liquid filled "gel capsules." The simple piercing device described in this invention makes available the contents of a gel capsule without the need to swallow it.

It should be noted that while the present invention is described herein with respect to the application of lubricant, it is to be understood that the present invention has other uses as well, including delivery of medicinal products, vitamins, nutrients, and other materials that from time to time need to be inserted into a body lumen. Accordingly, the invention is intended to encompass all such applications and uses, and is not to be limited to those described herein.

BRIEF DESCRIPTION OF THE DRAWINGS

The invention is described below in the detailed description of the preferred embodiments, which reference the following drawings accompanying this application.

FIG. 3A is an elevated perspective exploded view of an alternate embodiment for piercing a capsule;

FIG. 3B is an elevated perspective view of the alternate embodiment of FIG. 3a;

FIG. 4A is a cross sectional view of the embodiment of FIG. 3a taken along lines 4A-4A;

FIG. 4B is a cross sectional view of the embodiment of FIG. 3A in the closed position; and FIG. 4C is a cross sectional view of the embodiment of FIG. 3A showing the contents of a capsule being expelled by the device.

DETAILED DESCRIPTION OF THE PREFERRED EMBODIMENTS

The present invention is an applicator that delivers a bio-absorbable capsule of lubrication safely into a body lumen. Once inserted into the body lumen, the capsule can dispense the lubricant directly to the walls of the body lumen from within, thereby applying a thin layer of lubricant that can protect the lining of the body lumen from abrasion, tearing, or undue friction that can lead to discomfort.

Figure 1:
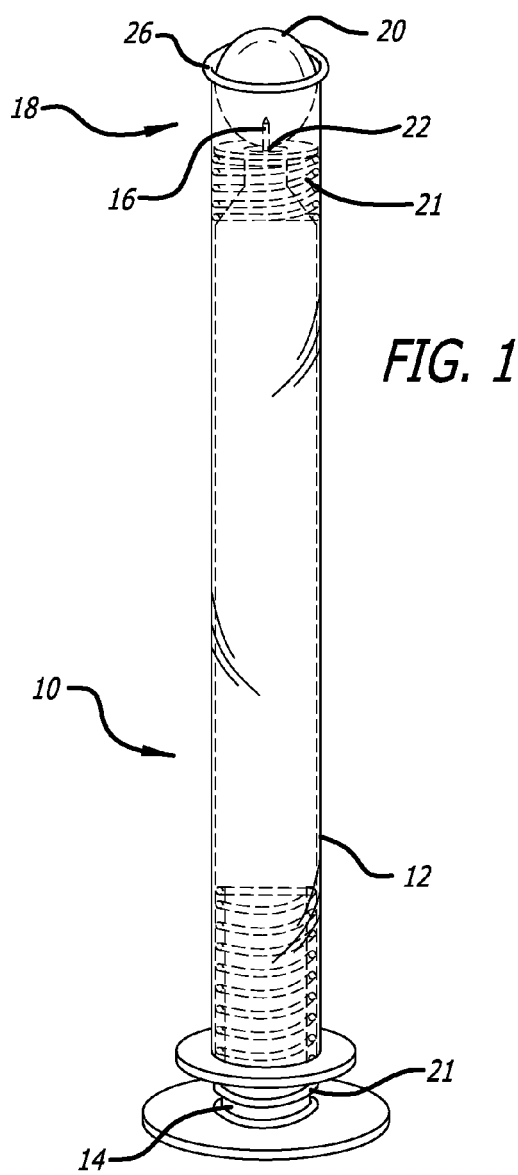
FIG. 1 an elevated, perspective view of a two-piece applicator of the present invention.

FIG. 1 illustrates a first preferred embodiment of the present invention characterized by a two-piece elongate cylindrical applicator 10 that has a first outer cylindrical sheath 12, and an internal cylindrical plunger 14 slidingly received within the outer sheath 12. The outer cylindrical sheath 12 is formed with a hemispherical receiving reservoir or cup 22 at a distal end 18 that can hold a lubricant capsule 20. The plunger 14 is equipped at a distal end with a piercing element 16 such as a pin, blade, prong, knife edge, or the like. In an alternate embodiment, there may be multiple piercing elements 16 such as a plurality of pins or knife edges. The piercing element 16 is disposed at a depth within the receiving cup 22 such that a capsule 20 once placed inside the receiving cup 22 would be impinged to the degree of rupture by the piercing element 16. The plunger 14, which can slide within the sheath 12, extends to the receiving cup at a distal end such that the capsule can be "pushed" out of the receiving cup by the plunger 14 when the plunger is fully actuated (i.e., depressed). The plunger may also have a spring at either the base or the distal end to assist in the ejection of the capsule. A narrowing at the distal end of the plunger 14 can be incorporated to aid in pushing the capsule out of the receiving cup 22. The plunger 14 may be biased in a deactivated condition by a spring 21. The user then depresses the plunger 14 against the biasing of the spring 21 to eject the capsule 20, providing greater control over the process and ensuring that the plunger 14 will disengage from the capsule as it withdraws and returns to the original position.

To employ the applicator 10, a user removes the preferably single use applicator from a sterile packaging, and places lubrication (or other type of) capsule 20 into the receiving cup 22 until the piercing element 16 ruptures or pierces the capsule. The applicator 10 is inserted into a body lumen such as a vagina or rectum. The applicator 10 is fully inserted therein, and the plunger 14 is actuated to push the capsule 20 from the receiving cup 22 and into the body lumen. The plunger 14 is designed so that no part of the plunge extends from the sheath 12 so that no tissue is harmed during the insertion or ejection process. The applicator 10 is then withdrawn from the body lumen, leaving the punctured bio-absorbable capsule 20 inside the body lumen. The puncture of the capsule 20 begins to leak its contents, be it lubricant or other delivery fluid, to the body cavity from within the body cavity (in situ). The capsule is preferably absorbed by the body, although it can be manually retrieved if desired after the act. This method of lubrication has the advantage of not having the lubricant wiped off during the insertion process, which is the case for externally applied lubrication methods and devices.

Figure 2:
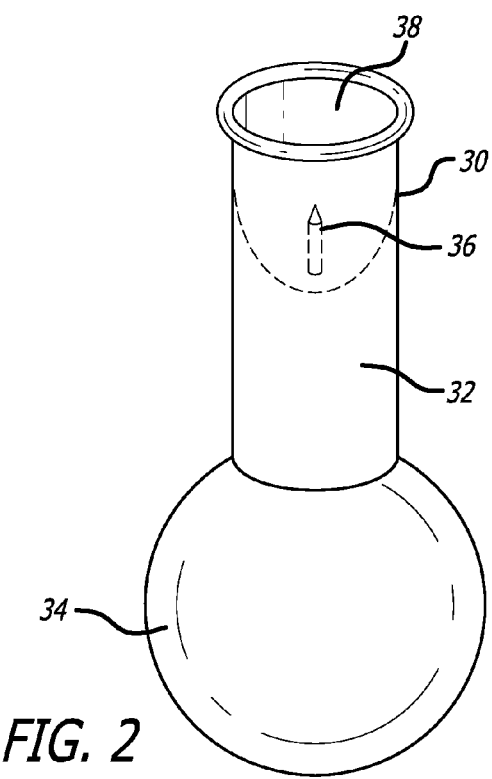
FIG. 2 is an alternate puncturing device for piercing a capsule.

FIG. 2 illustrates an alternate embodiment where the piercing tool 30 is a separate device from the applicator 10. Here, a cylindrical hollow tube 32 is mounted to a base 34, and includes a pin or piercing element 36 fixed at a depth spaced from the upper opening 38. A capsule 20 can be inserted directly into the cylindrical hollow tube 32 having a concave floor, until the capsule 20 is punctured, whereupon the capsule can be transferred to the applicator 10 or the contents otherwise emptied manually. This embodiment has the advantage of eliminating the use of a piercing element from the applicator, which is inserted into the body. However, in the first embodiment it is to be understood that the piercing element 16 cannot extend beyond the outer sheath 12 under any circumstances to prevent contact of the piercing element 16 with the tissue within the body lumen. The second embodiment may be easily utilized for the purpose of oral consumption of the contents of a gel capsule. A sequence can involve piercing the capsule, chewing the capsule, discarding the capsule's casing, and consuming the contents orally.

The capsule 20 can be any variety of soft gel capsules of various sizes, such as those similar to vitamin E soft gel capsules in consistency. When placed inside the body cavity, pressure on the outer surface from the surrounding tissue and muscle as a consequence of intercourse causes the capsule to leak lubricant through the piercing. The rate of dispersal is dependent upon the amount of pressure and the size of the opening, so care is needed to create an acceptable piercing that allows enough lubricant to be dispensed without releasing all of the lubricant at once. In this manner, a time release lubrication system is disclosed that can allow continuous lubrication throughout the process.

The term "capsule" is used generally herein to mean any device for storing lubricant or medicine. This would include packets, sponge-like material saturated with the delivery fluid, gels, balloons, or any frangible container that can be lanced, pierced, punctured, or otherwise opened to release the fluid. Moreover, as described above, the piercing instrument can be pin, nail, blade, barb, knife edge, or the like as long as it can successfully create an opening in the capsule to release its contents.

One advantage of the present invention is that it is hygienically suited to deliver the lubrication without introducing germs or bacteria. Each applicator 10 can be sold in a sealed package for single use only to prevent any unwanted organism, debris, or contaminant from being introduced into the body. The body lumen can be vaginal, anal, urinary, or any other body lumens where a fluid can be beneficially received. Also, the use of the piercing element 16, 36 allows intercourse to be initiated immediately, whereas other prior art systems requires that a medicinal or lubricating tablet dissolve before use, which can take up to a half hour or more. The present invention allows for immediate and time-release lubrication over the course of a session lasting thirty minutes or more. Once completed, the capsule does not need to be retrieved, but rather can safely dissolve in the body and be absorbed without consequence.

FIGS. 3 and 4 illustrate another embodiment for piercing a capsule. A box 40 having a pair of side walls 42, a floor 44, and a top surface 45 is formed with an internal wall 46 dividing the internal compartment therein into two smaller compartments. The top surface 45 includes a pivoting flap 47 that hinges centrally forward of the dividing wall 46, and can slide down within the box either on tracks or hinges. A block 48 sized to fit snugly inside the box 40 is formed with a recess 50 sized to capture and receive a frangible capsule 20 on a first side of the block 48. The recess 50 includes a pin 52 that can be used to puncture the capsule 20 as it enters the recess 50. To aid in controlling the capsule during the piercing process, the top surface 45 of the box 40 at the flap 47 can be squeezed by a user to capture and immobilize the capsule 20 in the box. That is, using pressure applied by a finger in the direction of arrow 49, the flap 47 can squeeze down on the capsule 20 while the block 48 is inserted into the box 40, sliding in and out like a match box sliding into and out of its outer structure. The inner wall 46 prevents the capsule from being pushed to the back of the box 40, ensuring proper engagement with the pin 52. When the block 48 is removed, the box 40 will contain a capsule 20 pierced by the pin 52, and retained at the open end of the box 40 as shown in FIG. 4C. By applying greater finger pressure in the direction of arrow 49, the contents 51 of the capsule 20 can be squeezed out of the capsule by the user without ever touching the capsule, thanks to the pinching movement of the pivoting flap 47. In this way, a capsule filled with a liquid or gel can be emptied by a user quickly and efficiently without touching either a pin or the capsule. This device can be used to open capsules for patients who cannot swallow pills and the like, allowing the contents of the capsule to be emptied onto a spoon, tongue, or the like.

The embodiments just described and depicted in the accompanying drawings are not intended to be limited, but rather exemplary of the modes and uses of the present invention. It is to be understood that various modifications and alternate uses are envisioned, and the present invention is intended to encompass all such modifications and alternate uses as would be understood by one of ordinary skill in the art.

I claim:
1. A device for piercing a capsule, consisting of:
a solid base having a first diameter;
a cylindrical hollow tube having a diameter smaller than the diameter of the solid base and a concave floor, the cylindrical hollow tube mounted to the solid base and having a longitudinal axis, the cylindrical hollow tube including an opening opposite the solid base; and a pin within the cylindrical hollow tube rigidly mounted to said concave floor and having a free end, said free end terminating at a height below the opening;

wherein a capsule can be manually inserted through said opening into the cylindrical hollow tube and punctured by the pin, and thereupon withdrawn from the cylindrical hollow tube through said opening.

\* \* \* \* \*